(12) United States Patent
Slepian (10) Patent No.: US 6,802,811 B1
(45) Date of Patent: Oct. 12, 2004

(54) SENSING, INTERROGATING, STORING, TELEMETERING AND RESPONDING MEDICAL IMPLANTS

(75) Inventor: Marvin J. Slepian, Tucson, AZ (US)

(73) Assignee: Endoluminal Therapeutics, Inc., Tuscon, AZ (US)

( * ) Notice: Subject to any disclaimer, the term of this patent is extended or adjusted under 35 U.S.C. 154(b) by 147 days.

(21) Appl. No.: 09/662,927

(22) Filed: Sep. 15, 2000

Related U.S. Application Data (60) Provisional application No. 60/154,637, filed on Sep. 17, 1999.

(51) Int. Cl.[7] .............................. A61B 5/00; A61K 9/22
(52) U.S. Cl. ................. 600/309; 604/890.1; 604/891.1; 600/325
(58) Field of Search ......................... 600/309–311, 325, 600/327, 339, 300, 332; 604/890.1, 891.1, 65–67

(56) References Cited

U.S. PATENT DOCUMENTS

| | | | |
|---|---|---|---|
| 4,146,029 A | * 3/1979 | Ellinwood, Jr. | 604/891.1 |
| 4,364,385 A | 12/1982 | Lossef | |
| 4,399,821 A | * 8/1983 | Bowers | 600/301 |
| 4,505,710 A | * 3/1985 | Collins | 604/891.1 |
| 4,705,503 A | * 11/1987 | Dorman et al. | 604/504 |
| 5,056,530 A | 10/1991 | Butler et al. | |
| 5,411,551 A | 5/1995 | Winston et al. | |
| 5,511,428 A | 4/1996 | Goldberg et al. | |
| 5,512,882 A | 4/1996 | Stetter et al. | |
| 5,526,703 A | 6/1996 | Aslam et al. | |
| 5,536,963 A | 7/1996 | Polla | |
| 5,544,651 A | 8/1996 | Wilk | |
| 5,709,225 A | 1/1998 | Budgifvars et al. | |
| 5,769,893 A | 6/1998 | Shah | |
| 5,797,898 A | 8/1998 | Santini et al. | |
| 5,807,258 A | 9/1998 | Cimochowski et al. | |
| 5,807,259 A | 9/1998 | Nakamura et al. | |

(List continued on next page.)

FOREIGN PATENT DOCUMENTS

| | | |
|---|---|---|
| EP | 0850654 A1 | 7/1998 |
| WO | WO 91/01689 A1 | 2/1991 |
| WO | WO 92/21307 A1 | 12/1992 |
| WO | WO 98/29030 A1 | 9/1998 |
| WO | WO 99/64580 A1 | 12/1999 |

*Primary Examiner*—Mary Beth Jones
*Assistant Examiner*—Matthew Kremer
(74) *Attorney, Agent, or Firm*—Pabst Patent Group LLP

(57) ABSTRACT

Implants and implants, including sensors responsive to pressure, fluid flow, concentration of analytes, pH and other variables, including a feedback loop and means for modifying the implant after placement in a patient in response to measurements made using the sensors, have been developed. These are particularly useful in cardiology, where the implants contain one or more sensors responsive to variables which change over time, for example, pressure which is indicative of changes in fluid flow and diameter of the vessel in which the implant has been placed. Feedback from the sensor(s) either directly, or indirectly via monitoring means external to the patient, signal changes that may be required, such as expansion of the implant in the case where the vessel diameter changes over time or the implant becomes unstable or migrates. In another embodiment, the implant contains a bioactive, prophylactic, diagnostic or pH modifying agent wherein the implant is formed of a temperature or pH responsive material so that the agent is released when the temperature or pH is altered. These systems can also be used to connect a patient to a remote data storage system, such as the internet or a computer accessible through devices such as PDA (Palm Pilot systems), phone system devices (portable phones, answering services, beepers, office fax machines), that the physician or nurse can monitor or use to interact remotely with the implant.

18 Claims, 4 Drawing Sheets

U.S. PATENT DOCUMENTS

| | | | |
|---|---|---|---|
| 5,833,603 A | 11/1998 | Kovacs et al. | |
| 5,833,623 A | 11/1998 | Mann et al. | |
| 5,865,972 A | 2/1999 | Buffle et al. | |
| 5,883,310 A | 3/1999 | Ho et al. | |
| 5,898,004 A | 4/1999 | Asher et al. | |
| 5,928,248 A | 7/1999 | Acker | |
| 5,938,607 A | 8/1999 | Jago et al. | |
| 5,964,993 A * | 10/1999 | Blubaugh, Jr. et al. | 204/403 |
| 6,015,387 A | 1/2000 | Schwartz et al. | |
| 6,053,873 A | 4/2000 | Govari et al. | |
| 6,091,980 A | 7/2000 | Squire et al. | |
| 6,092,530 A * | 7/2000 | Weissman et al. | 128/899 |
| 6,201,980 B1 * | 3/2001 | Darrow et al. | 600/347 |
| 6,248,080 B1 * | 6/2001 | Miesel et al. | 600/561 |
| 6,312,378 B1 * | 11/2001 | Bardy et al. | 600/300 |

* cited by examiner

SENSING, INTERROGATING, STORING, TELEMETERING AND RESPONDING MEDICAL IMPLANTS

This application claims priority to U.S. Ser. No. 60/154,637 filed Sep. 17, 1999.

BACKGROUND OF THE INVENTION

This disclosure is generally in the area of implants which include sensors capable of detecting or interrogating physical, cellular, and other variables, including means for collecting, amplifying, storing and telemetering information as well as a feedback loop and means for modifying the implant after placement in a patient in response to measurements made using the sensors.

Medical implants have been used for many years in interventional radiology, gastroenterology, urology and cardiology and other fields of medicine and surgery. In general, these devices are static and not interactive, i.e., they are implanted for a particular purpose and no change occurs, save for bystander corrosion or biodegradation, over time or for removal in the event a problem develops. Typically conventional implants are fashioned from medical grade stainless steel, compatible polymers, e.g. Dacron™ or Teflon™, or ceramics. More advanced implants have been developed using shape memory metals and polymers. Shape memory is the ability of a material to remember its original shape, either after mechanical deformation, or by cooling and heating. These materials have been proposed for various uses, including vascular implants, medical guidewires, orthodontic wires, etc.

Recently, in an attempt to move implants from being simple structural or augmentative, non-interactive devices, modifications have been made to include a sensor, for example, sensors for cardiac activity or sensors for monitoring blood flow. The sensors measure flow, pressure and/or strain. Most are not remotely "interrogatable", which is understood to mean that data cannot be extracted remotely, after implantation in a body. Some are remotely interactive, however. For example, particularly with the pacemaker patents, batteries can be re-charged non-invasively. Some sensors are interactive at the site of implantation, but not remotely. Most require some type of "hard-wiring" to either program the device or to extract data. U.S. Pat. No. 5,411,551 to Winston, et al., describes a stent that includes a sensor located on the inside of the expandable stent wall that is directly connected to a remote monitoring device. U.S. Pat. No. 6,091,980 to Squire, et al., describes a stent including multiple conductive pads to generate a signal when the stent slips or moves from the original position.

An example of a stent which includes a remotely accessible sensor to assist in locating the stent is described in EP 0850654 by Schneider (USA) Inc. U.S. Pat. No. 5,807,259 to Cimochowski, et al., U.S. Pat. No. 6,053,873 to Govari, et al., and U.S. Pat. No. 6,015,387 to Schwartz, et al. describe a device which is implantable to monitor flow and/or pressure in a vessel, graft or prosthetic. The '259 and '873 pressure sensors include a radio coil for remote access of the data which is transmitted as ultrasonic waves by a transducer. The '387 sensor generates an electromagnetic, ultrasonic and/or radio frequency signal indicative of the rate of blood flow in the associated vessel. U.S. Pat. No. 5,833,603 to Kovacs, et al. describes an implantable transponder including a sensor for temperature, strain, pressure, magnetism, acceleration, ionizing radiation, acoustic waves, or chemicals, where the sensor can be associated with an implanted prosthetic or graft. Data is transmitted to a remote reader. U.S. Pat. No. 5,709,225 to Budgifvars, et al., assigned to Pacesetter AB, describes a medical implant containing a magnetic field detector with a capacitative sensor detecting changes in the presence of a magnetic field, and means for generating a remotely-detectable signal, for use in determining an appropriate medical therapy. U.S. Pat. No. 5,928,248 to Acker describes a stent including a system which transmits non-ionizing fields between a transducer or transducers on the probe and external transducers, to aid in positioning of the stent.

None of these devices, however, are responsive to the data which is collected by the sensors. None of these devices incorporates means of repeated or interval or programmed interrogation, via either intrinsic or extrinsic interrogative means. None of these devices incorporates within the device means for signal processing and interpretation. None of these devices includes means for raw or processed data storage. None of these devices has incorporated intrinsic or proximate means for change, i.e. alteration of the local environment or local or distant therapy as a result of gathered information. Further, none of these devices has the ability to telemeter and interact with data transmission or communication means which exist as single or mutiple e.g. nested, loops of information transfer. Therefore it is an object of the present invention to provide a method, devices, and systems incorporating such devices, for implantation in a patient wherein the implant includes means for collection, and/or processing and/or storage of data.

It is another object of the present invention to provide a method, devices, and systems incorporating such devices, for implantation in a patient wherein the implanted device includes means for telemetry or communication of data for subsequent interaction with data transmission or communication means, in single or mutiple such as "nested", loops of information transfer.

It is another object of the present invention to provide a method, devices, and systems incorporating such devices, for implantation in a patient wherein the implant includes means for responding, such as mounting of a therapeutic action, on the basis of either local data collected or external dependent or independent signals.

SUMMARY OF THE INVENTION

Implantable devices (i.e., "implants"), including sensors for data measurement, and/or data analyzers, and/or data storage means, and/or data telemetry/transmission means including means for communication at mutiple levels of isolated or nested levels of information transfer have been developed. These devices may have incorporated means for modification of the implant or mounting a response, e.g. local or systemic drug delivery, in response to measurements made using the sensors. These are particularly useful in urology, hepatology or cardiology, where the implants contain one or more sensors responsive to variables which change over time, for example, pressure which is indicative of changes in fluid flow and diameter of the ureter, biliary duct or vessel in which the implant has been placed. Feedback from the sensor(s) either directly, or indirectly via monitoring means external to the patient, signal changes that may be required, such as expansion of the implant in the case where the tissue lumen diameter changes over time or the implant becomes unstable or migrates. In another embodiment, the implant contains a bioactive, prophylactic, diagnostic or pH modifying agent. In one embodiment, the implant is formed of a temperature or pH responsive material so that the agent is released when the temperature or pH is altered.

These systems can also be used to connect a patient to a remote data storage or manipulation system, such as a watch-like device, small portable device, intra or extradermal implant, phone system devices (portable phones, answering services, beepers, office fax machines), portable computer, personal digital assistant (PDA, e.g., Palm Pilot™ systems), or to the internet (world wide web) or a computer accessible through devices that the physician or nurse can monitor or use to interact remotely with the implant.

BRIEF DESCRIPTION OF THE DRAWINGS

As shown in FIG. 4a, the sensor transmits information to a computer with a display means. As shown in FIG. 4b, the sensor again transmits to a computer which posts the information to a web page on an internet site. As shown in FIG. 4c, the sensor transmits to a repeater unit worn by the patient, or in close proximity. The repeater unit amplifies outgoing and incoming transmissions, and is in communication with an outside computer.

DETAILED DESCRIPTION OF THE INVENTION

I. Smart Responsive Implants or Implants
A. Implants and Implants

As generally understood, implants may be of a wide variety of shapes and configurations. In general the shape will be dictated by the location of internal implantation as well as function. Implanted devices may be of many forms. For example, such devices might include various types of stents, such as endoluminal stents, stent-grafts, grafts (including by-pass grafts), rings, hooks, sutures, wires, and tissue conduits. Such devices may be implanted in locations such as arteries, veins, venous fistulas, bile ducts, the ureter, fallopian tubes, and artificial spaces created surgically. Implants as contemplated herein might be implanted by various methods including needle, trocar, percutaneous implantation, surgical implantation, and endoscope. Implants would preferably be made of materials which did not provoke an immune response, and which resisted fouling, if tissue ingrowth were not desired.

In this regard, the function of the implant may be strictly to sense, to sense and store data, to sense, store and amplify or otherwise process data or to sense, store, process and transmit or otherwise communicate the information via electrical, electromagnetic, optical, radio, chemical, ultrasonic, thermal or other means. In addition to diagnostic as well as transmission functions, the implant may have innate support, augmentative or therapeutic functions to directly modulate the contiguous implant zone tissue or alter function in the peri-zone or at a distance.

Diagnostic implants may be simple spheres, pellets, wafers, slivers, chips, or weaves, fabrics or stamp-like arrays of these or other shapes. An example of simple support implants are tubes made of metal or plastic that is inserted into a body lumen, vessel or passage to keep the lumen open and prevent closure due to stricture or external compression. Implants are commonly used to keep open bile ducts for treatment of pancreatic cancer or cholangiocarcinoma, the oesophagus for strictures or cancer, the ureters to maintain drainage from the kidneys or blood vessels, i.e. coronary or peripheral arteries.

As used herein, implants can also refer to prosthetics for repair or replacement of tissue, connective tissue or bone, where the device supports or seals an injury due to surgery, trauma or disease, or which is seeded with cells to repair or replace tissue or an injury thereto.

Implants are generally made of a biocompatible material, which may be biodegradable or more typically, non-biodegradable. Exemplary materials include metals such as titaniwn, nitinol and surgical stainless steel, ceramics, and synthetic polymeric materials. Non-biodegradable materials include polyethylene, TEFLON™ and pyrolytic carbon. Preferred biodegradable polymers include polylactic acid, polyglycolic acid, polycaptolactone and copolymers thereof.

B. Sensors

One or more sensors can be positioned in, on or as part of the implant. These can be used to measure temperature, mechanical forces such as stress and strain, pressure, and force; fluid flow properties such as flow rate and shear, electromagnetic fields, and chemical factors or variables, including pH, ion concentration, enzymes (presence of, activity of, or use of to measure other elements), and analyte concentrations or distributions. Sensors can also be used to monitor alterations in concentration or distribution of cells or tissues based on volume, or properties of the cells or tissue, such as stiffness, elasticity, surface adhesivity, and surface charge, changes in metabolic products, changes in antigenicity or cell surface expression, and the presence of foreign depositions including inorganic, organic and microbial materials.

Examples of applications of these sensors include measuring changes in weight by measuring changes in adipocyte cell volume and fat mass/lipid across a region such as a limb and measuring tissue fibrosis as changes in stiffness of a tendon, skin stiffness or muscle tension or rigidity.

Other applications relating to fouling of the implant over time, include measurements relating to protein deposition or formation of a bacterial film on the biliary stent, increase in calcification of a urinary stent, and neointimal thickening of an arterial stent, resulting in an increase in thickness, mass and wall shear.

Sensors can be located on the surface, inside a hollow or porous wall of the implant, or inside a device in communication with the body tissue via a conduit to the implant (solid, hollow, or porous). These sensors primarily include one or more of four classes of transducers: potentiometric, amperometric, optical, and physiochemical. An amperometric sensor monitors currents generated when electrons are exchanged between a biological system and an electrode. Blood glucose sensors frequently are of this type. Potentiometric sensors measure changes in potential between electrodes positioned apart from each other in an area over which a measurement is to be made, for example, as described by U.S. Pat. No. 6,091,980 to Squire, et al.

The sensors may include means for transmitting a signal to monitoring means or directly to actuating means. The means for transmitting a signal may be hard wired or transmitted via radio waves or magnetic or mechanical means.

Sensors which may be used include those described in U.S. Pat. No. 5,807,259 to Cimochowski, et al.; U.S. Pat. No. 5,833,603 to Kovacs, et al. and U.S. Pat. No. 5,709,225 to Budgifvars, et al. U.S. Pat. No. 5,807,258 describes ultrasonic sensors for monitoring the condition of a vascular graft. A parameter indicative of the status of fluid flow is remotely monitored in a vessel, a natural graft, or a synthetic graft. One or more transducers are provided either in a wall of a synthetic graft or adjacent to a vessel or natural graft to monitor the parameter. A conformal array transducer or a tilted element is used to monitor fluid flow or velocity through the graft or vessel based on the effect of the fluid on ultrasonic waves produced by the transducers. The conformal array transducer comprises a plurality of elements that curve around the graft or vessel and are excited with an input signal provided by an implantable electronics circuit, producing ultrasonic waves that propagate into the fluid flowing within the graft or vessel. Transit time or Doppler measurements are made using an appropriate number of these transducer to determine either fluid flow or velocity. Various implantable electronic circuits are provided that enable a selected transducer to be driven and to receive an ultrasonic signal or a pressure signal indicative of the status of fluid flow monitored by the transducer. The implanted electronic circuit can be connected to an implanted radio frequency (RF) coil. An external coil that is connected to a power supply and monitoring console is coupled to the implanted RF coil to convey power and receive data signals from the transducer that are indicative of the parameter being monitored.

U.S. Pat. No. 5,833,603 describes implantable transponders utilizing temperature sensors, strain sensors, pressure sensors, magnetic sensors, acceleration sensors, ionizing radiation sensors, acoustic wave sensors, chemical sensors including direct chemical sensors and dye based chemical sensors, and photosensors including imagers and integrated spectrophotometers. The transponder includes an energy coupler for wirelessly energizing the device with a remote energy source, and a control circuit for controlling and accessing the biosensor and for storing identifying data. The energy coupler can be an inductive circuit for coupling electromagnetic energy, a photoelectric transducer for coupling optical energy, or a piezoelectric transducer for coupling ultrasonic energy. The control circuit can be configured to delay, either randomly or by a fixed period of time, transmission of data indicative of the sensed parameter value to thereby prevent a data collision with an adjacent like device.

U.S. Pat. No. 5,709,225 describes a magnetic field detector with a sensor whose capacitance changes in the presence of a magnetic field with a predefined strength, and a capacitance-controlled unit connected to the sensor. The capacitance-controlled unit sends a measurement signal to a detection unit. If a measurement signal parameter affected by capacitance exhibits a specific change over a predefined period of time, a detection signal is generated by the detection unit to indicate the presence of a magnetic field. The sensor's capacitance also changes when the sensor moves, and this is utilized for measuring activity in an activity measurement circuit connected to the capacitance-controlled unit and for generating an activity signal on the basis of the measurement signal.

U.S. Pat. No. 5,865,972 describes integrated electrochemical microsensors for chemical analysis, allowing the determination of concentration or concentration profile of at least one chemical compound with small size or molecular weight, under organic, inorganic, neutral or ionic form in an aqueous environment. The microsensor comprises an array of microelectrodes, assembled on a chip supported by an isolating substrate, and linked with at least one conductor protected by an insulating layer to a contact allowing the connection to a measuring apparatus. U.S. Pat. No. 5,898,004 discloses crystalline colloidal array sensors. The hydrogels are capable of shrinking and swelling in response to specific stimuli applied thereto. As the hydrogels shrink or swell, the lattice structure of the CCA embedded therein changes, thereby changing the wavelength of light diffracted by the CCA. Thus by monitoring the change in diffracted wavelength, the concentration of a stimulus is determined. The gels can be modified to sense numerous different stimuli. U.S. Pat. No. 5,883,310 describes a micromachined hot-wire shear stress sensor. The micromachined hot-wire anemometer having fast response times and higher sensitivities than conventional hot-wire anemometers is provided by micromachining doped polysilicon wires carried on silicon supports cantilevered from a substrate including one or more insulating layers disposed between said substrate and supports. The micromachined polysilicon hot-wire anemometer is fabricated using surface micromachining techniques. A shear stress sensor is micromachined to define a thin diaphragm over a cavity defined in a substrate underlying the diaphragm. The cavity is evacuated, sealed, and a thermistor disposed over the diaphragm. The thermistor is thus thermally insulated from the substrate and provides a low profile shear stress sensor for measuring flow rates in boundary layers above a flow surface. See also U.S. Pat. Nos. 5,511,428, 5,512,882, 5,526,703, 5,536,963, 6,053,873, 5,411,551 and EP 0 850 654 A1.

Sensors may be micromachines manufactured using MEMS technologies and microfabrication means, for example as described in U.S. Pat. No. 5,797,898 to Santini, et al. or WO 99/64580 by Georgia Tech Research Corporation. As such sensors may be incorporated into the microstructure of a fabricated chip. A single, multiple or an array of chips may be fashioned and fabricated onto the body of the implant. These arrays may be on the ectoluminal or endoluminal surface of a cylinderical or spherical configuration.

The sensors can also include means for storage of data. Silicon wafer prepared using standard photolithographic or other manufacturing techniques can be included in the sensors for storage of data over time, which can be accessed routinely during the time the sensor is implanted, or downloaded after removal of the implant containing the sensor.

C. Monitoring Means

A number of devices, both external and internal, can be used to receive and transmit signals from the sensors to the actuators. These may be radio transponders, light, or sound wave receivers and transmitters, or hard wired into the devices.

For example, the ultrasonic sensor described in U.S. Pat. No. 5,807,258 can be used to monitor the condition of a vascular graft. One or more transducers are provided either in a wall of the implant or adjacent to the implant to monitor the parameter. A conformal array transducer or a tilted element is used to monitor fluid flow or velocity through the implant based on the effect of the fluid on ultrasonic waves produced by the transducers. The conformal array transducer comprises a plurality of elements that curve around the implant and are excited with an input signal provided by an implantable electronics circuit, producing ultrasonic waves that propagate into the fluid flowing within the graft or vessel. Transit time or Doppler measurements are made using an appropriate number of these transducer to determine either fluid flow or velocity. Various implantable electronic circuits are provided that enable a selected transducer to be driven and to receive an ultrasonic signal or a pressure signal indicative of the status of fluid flow monitored by the transducer. The implanted electronic circuit is connected to an implanted radio frequency (RF) coil. An external coil that is connected to a power supply and monitoring console is coupled to the implanted RF coil to convey power and receive data signals from the transducer that are indicative of the parameter being monitored.

In a preferred embodiment, the monitoring means will be connected to data communication and/or storage means, to provide for online monitoring of the stored data. Data can be stored in the implant or at a remote location. Means to access this information, and to download the data, are integrated so that the attending physician or nurse can monitor the patient long term, and provide corrections to the implant if necessary. As noted above, the storage means may be in the form of a silicon chip in the sensor or implant. Alternatively, the monitoring means connected to the sensor(s) includes data storage means. This will typically be a computer, which may be connected to the internet or phone lines, so that data can be remotely accessed through phone lines (including beepers), other computers, or personal digital assistant (PDAs).

D. Actuators

Actuators will typically consist of micromachined devices, or form a part of the implant. Alternatively, they can be in the form of reservoirs, switches or valves.

U.S. Pat. No. 5,536,963 describes a micromechanical structure or microactuator based upon the piezoelectric, pyroelectric, and electrostrictive properties of ferroelectric thin film ceramic materials such as PZT with a thickness between 0.1 and 10 micrometers, and method of manufacture thereof. The thin film ceramic material is sandwiched between first and second electrodes and may contain an intermediate electrically insulating thin film. This structure with electrodes is formed on a deformable or movable structure integral to a semiconductor or bulk ceramic substrate. Electrical connection is established between the upper and lower electrodes. A potential difference or voltage is established between the electrical interconnection points to produce a force, movement, or mechanical deformation. The patent also discloses method for making such micromechanical structures or microactuators.

The implant may function as a conduit for fluids, solutes, electric charge, light, or other materials. In one embodiment, hollows within the implant walls, or the implant itself, can be filled with a substance, such as a gel, that has a sensing functionality associated with it. In an application for sensing based on binding to a substrate or reaction mediated by an enzyme, the substrate or enzyme can be immobilized in the interior of the implant, to create an integral needle/sensor.

Wave guides can be incorporated into the device to direct light to a specific location, or for dection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

E. The System

The sensor detects one or more physical properties of its surrounding environment, and provides an output signal of the detected physical property to the control circuit. The control circuit then sends data indicative of the detected physical property to a remote reader with an energy coupler or with a different energy coupler. The control circuit can be encoded with identifying data before or after implantation. Such data may relate to the sensor, the patient into which the device is implanted or both. The identifying data may also be a unique tag for accessing data stored in a remote data bank, such as a personal computer or a memory device in a remote reader. Hence, even after implantation of the implant with sensor(s), identifying data can be retrieved from control circuit in a non-invasive manner, as can data corresponding to sensed parameter values.

Ultrasonic and optical coupling can be used with a transponder for energizing and providing command signals to the transponder, and for transmitting identifying data, including unique tags, from the transponder to a remote reader. A transponder can include more than one energy coupler, particularly where it is advantageous to energize the sensor with one form of energy, and transmit data using another. Where desirable, a third energy coupler can also be used to receive control commands from an external source using either the same or different forms of energy as those used for energizing the transponder and transmitting data therefrom.

Figure 1:
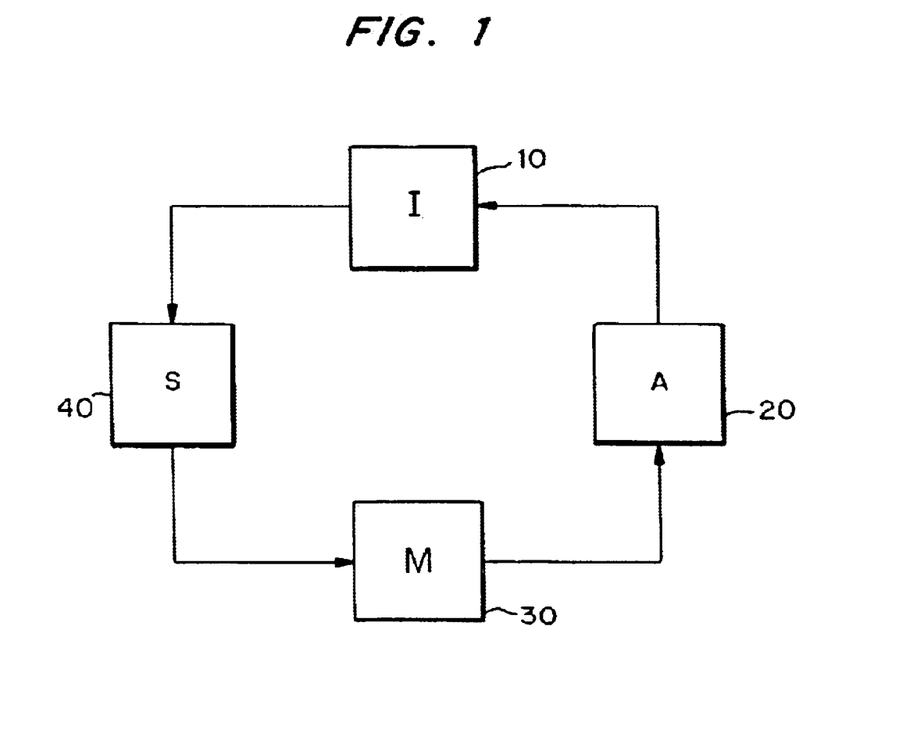
FIG. 1 is a flow diagram of the implant (I), sensors (S), monitoring means (M), and actuators (A), showing the feedback path of the devices described herein.
Figure 2:
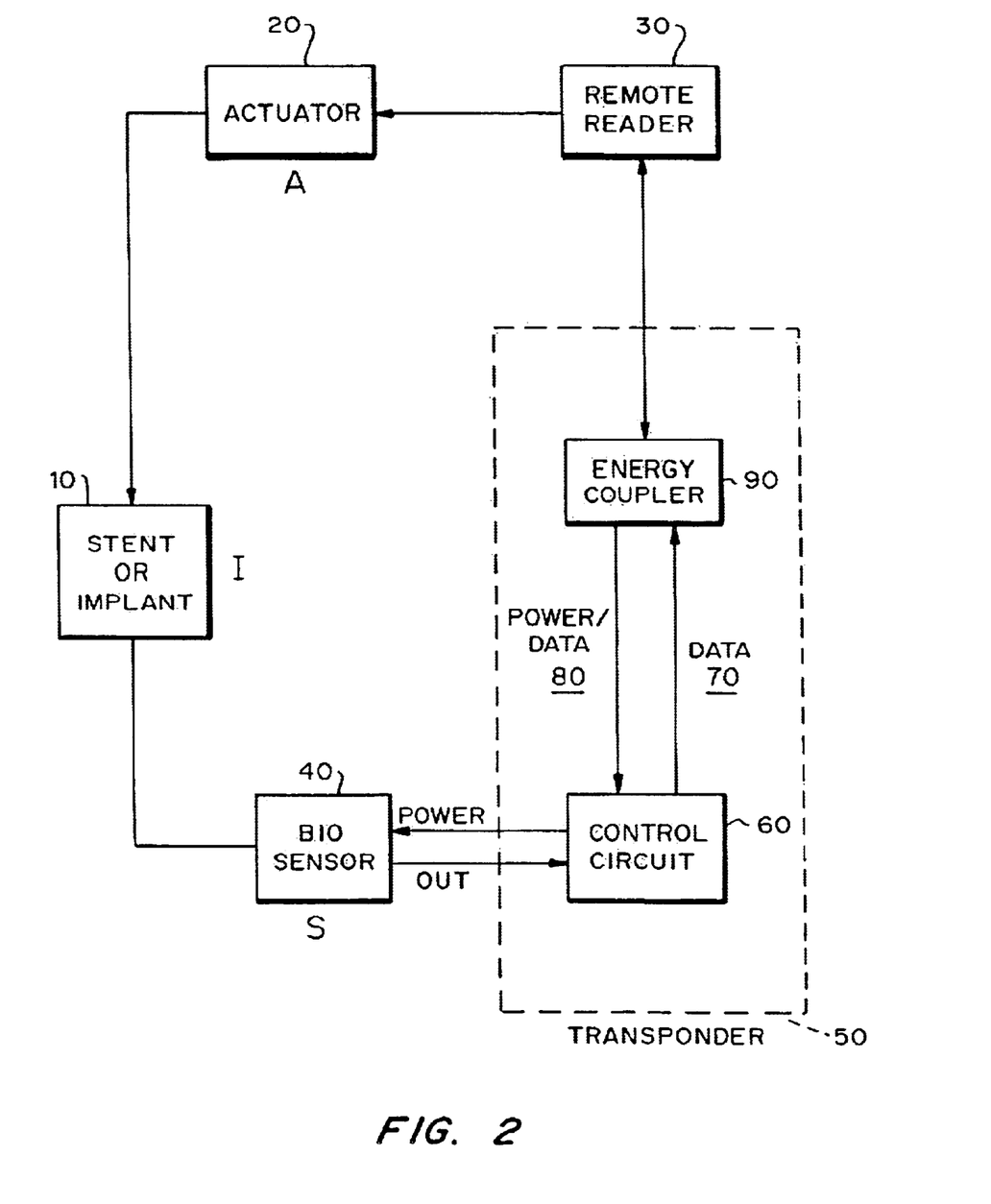
FIG. 2 is a flow diagram of a implant I connected to a sensor S and transponder including an energy coupler and control circuit connected to a remote reader (or monitoring device) which sends a signal to the actuator to act upon the implant.
Figure 3:
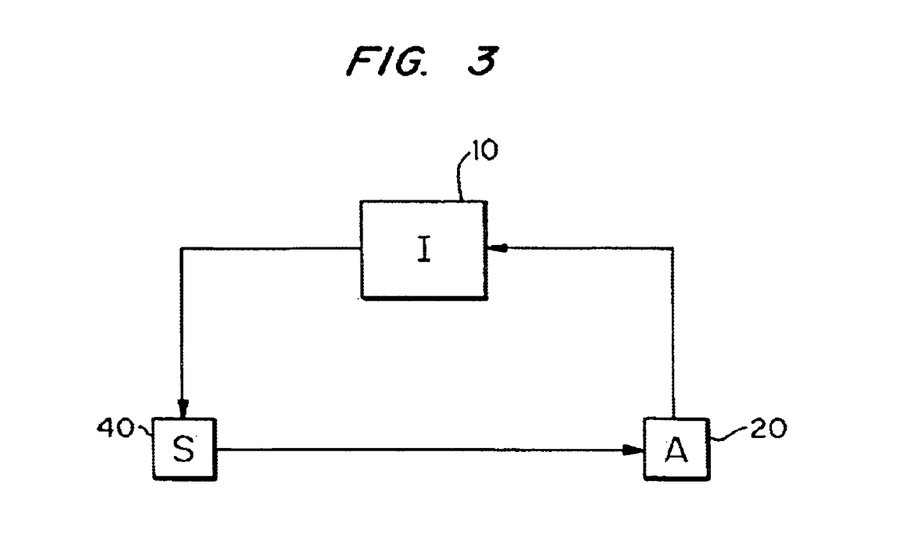
FIG. 3 is a flow diagram of a simple embodiment, in which the system includes the implant, sensor and actuating means.

FIG. 1 is a flow diagram showing the interaction between the implant (a), sensor(s) (S), monitoring means (M), and actuating means (A), in the most typical embodiment. FIG. 2 is a flow diagram of a more complex embodiment, wherein the implant I is connected to a sensor S and transponder including an energy coupler and control circuit (referred to jointly as a biosensing transponder, as described for example, in U.S. Pat. No. 5,833,603). This is in turn connected to a remote reader (or monitoring device) which sends a signal to the actuator to act upon the implant. FIG. 3 is a flow chart of the simplest embodiment, in which the system includes the implant, sensor and actuating means.

One embodiment of system described herein is a telemetry system of nested communication loops. A sensor may communicate with a contiguous device, such as an actuator associated with an implanted device, an implanted device, or with a free-standing electronic communication device, or with a computer accessing the world wide web. In one embodiment of the invention, all these devices may communicate with each other, or in specific hierarchies.

The processing units of implants might be an integrated circuit with dedicated functions. The sensing units might also be specialized integrated circuits, known colloquially as "biochips".

Included with the implant may be a sensor that generates a signal in response to conditions detected by the sensor. Included with the sensor is a memory means for storing information regarding the conditions, transmitting and receiving means, actuating means for carrying out a response by the implant to conditions sensed by the sensor, and a power source. The sensor optionally includes an information processing means. Various sensors may be employed to detect mechanical, sonic, electrical, chemical, temperature, and optical conditions, among others. Mechanical conditions sensed might include pressure, dimension, flow, and vibration. The sensor generates a signal after sensing said conditions, which signal is sent to the transmitter, or which signal may be stored in the memory means. The transmitter might transmit the signal by optical fiber, by wire, or wirelessly, using power from the power source. The sensor might be programmed to transmit continuously, but more likely it would be programmed to transmit on a regular schedule to conserve energy, and transmit more frequently upon the sensing of a certain condition. In one embodiment of the invention, the power source might be a battery. Optical transmission might be through optical fibers, while wired transmission might be though electrical transmission over an electrical conductor. Wireless transmission might take place through radio wave signals, or ultrasonically. In one embodiment of the invention, a standard communication protocol might be employed, such as a version of BLUETOOTH™, which is promulgated by the Bluetooth Special Interest Group (which includes 3Com, IBM, Intel, Lucent, Microsoft and Nokia, among others). In one embodiment of the invention, the sensor may both transmit and receive information.

In one embodiment, the person having the implant might wear on his person, or keep in close proximity, a repeater unit to strengthen the signal generated by the implanted sensor. In that manner the sensor could include a smaller power source, and thus be more compact. The repeating unit might also include a more sensitive receiver than the implant unit, and thus aid in transmissions back to the implanted sensor.

In one embodiment, a person such as a physician, or the patient could monitor the transmissions from the sensor by means of a portable device, such as a personal digital assistant, portable computer, internet appliance, cellular telephone, two-way radio, web-enabled television, or watch communicator. In another embodiment, a person might monitor the transmissions from the sensor by using an ordinary telephone linked to a command menu, or which has speech to text and text to speech capabilities allowing the user to request the desired presentation of data. In another embodiment, the sensor could transmit to a receiving unit which would post the information sent by the implant sensor to a web page, accessible by the patient or the physician. In another embodiment, the web page would be accessible only by password, and the ability to issue commands to the device might be further password-protected.

In one embodiment, a person monitoring the information sent by the implant sensor could transmit information back to the implant sensor. Such information might be commands to be carried out through the actuator. For example, if a sensor on a stent detected a mechanical narrowing of the internal passage, a physician might read that information from the web posting, and send a command back to the stent to the actuator to widen the passage. In that case the actuator might be a small mechanism in the stent that forces the stent to open more widely. In another example, an optical sensor might detect the presence of unwanted cellular accumulation in the interior of the stent. A physician might read that information, and send a command to the stent to the actuator to release a small amount of a protease to dissolve the accumulation. In that case the effector would be a reservoir containing protease, where a release mechanism on the reservoir could release a measured amount of protease. In another embodiment, the implant might be an implant in a deep abscess in a patient. The implant might be an bandage, including expandable foam to promote healing. The sensor might monitor local temperature to assess the presence or absence of infection. A monitoring physician, observing a tell-tale warming, might direct the actuator to release a certain amount of an antibiotic solution.

A person, such as a physician, might also communicate with the sensor directing it to issue an alert if certain conditions were sensed. For example, sensing of too great a narrowing of a vessel, or an erratic flow rate through a vessel, might be conditions for which a physician might direct the sensor to send an alert.

Depending upon the amount of information recorded by the sensor, it might be directed to download the information through the transmitter for permanent storage outside the sensor at various times. This would free up memory space in the sensor.

In another embodiment, the information processing means may be programmed to have the actuator carry out certain actions in response to the sensing of certain conditions. This programming might be effected through transmissions by a physician. For example, the physician might program the sensor, by remote transmissions, to carry out a certain schedule of release of an antibiotic. Alternatively, the physician might program the sensor to release antibiotic at one schedule if a certain temperature were sensed, and another, more infrequent schedule, if another temperature were sensed. For instance, the sensor might be programmed to have the actuator release 0.5 ml of penicillin per ten hours if a temperature of 102 degrees Fahrenheit were sensed, but to reduce that schedule to 0.3 ml of penicillin per twenty hours when the temperature declined to 99.9 degrees Fahrenheit.

Figure 4A:
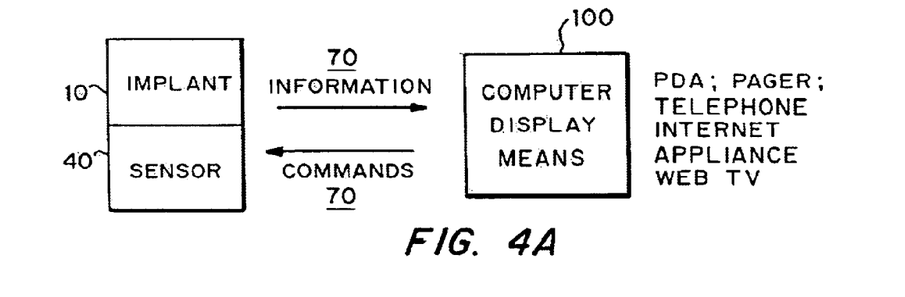
FIGS. 4a–4c are schematics of the system connected to remote communication and/or data storage means.

As shown in FIG. 4a, in one embodiment of the system, the implant coupled to the sensor transmits information to a computer with a display means. The computer might be any number of devices capable of receiving information, including personal digital assistants, pagers, telephones, internet appliances, watch communicators, and web-enabled televisions, as discussed above. The communication might occur by some standard protocol, such as BLUETOOTH™. The user could transmit commands or inquiries directly back to the implant.

Figure 4B:
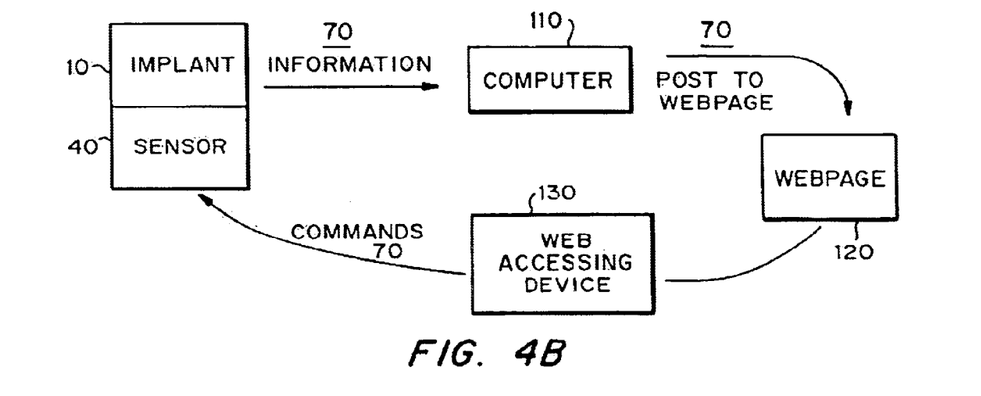

As shown in FIG. 4b, the implant coupled to the sensor again transmits to a computer. However, the computer in this case might post the information to a web page on an internet site, probably password-protected. A patient or physician could access this information by using a communications device to access the web site. Commands could be sent directly to the implant from the accessing device, or via the web page and prompts on the web page (FIG. 4b only shows the direct command route).

Figure 4C:
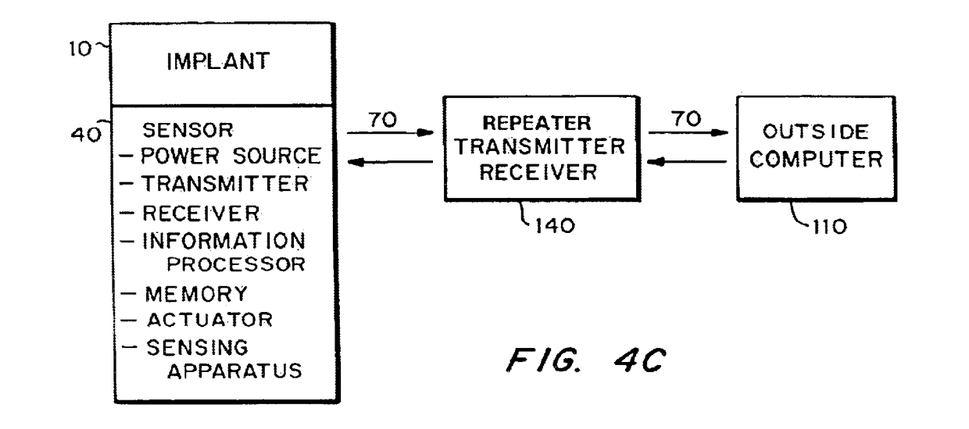

As shown in FIG. 4c, the implant is coupled to a sensor, which transmits to a repeater unit worn by the patient, or in close proximity. The repeater unit amplifies outgoing and incoming transmissions, and is in communication with an outside computer.

Figure 5:
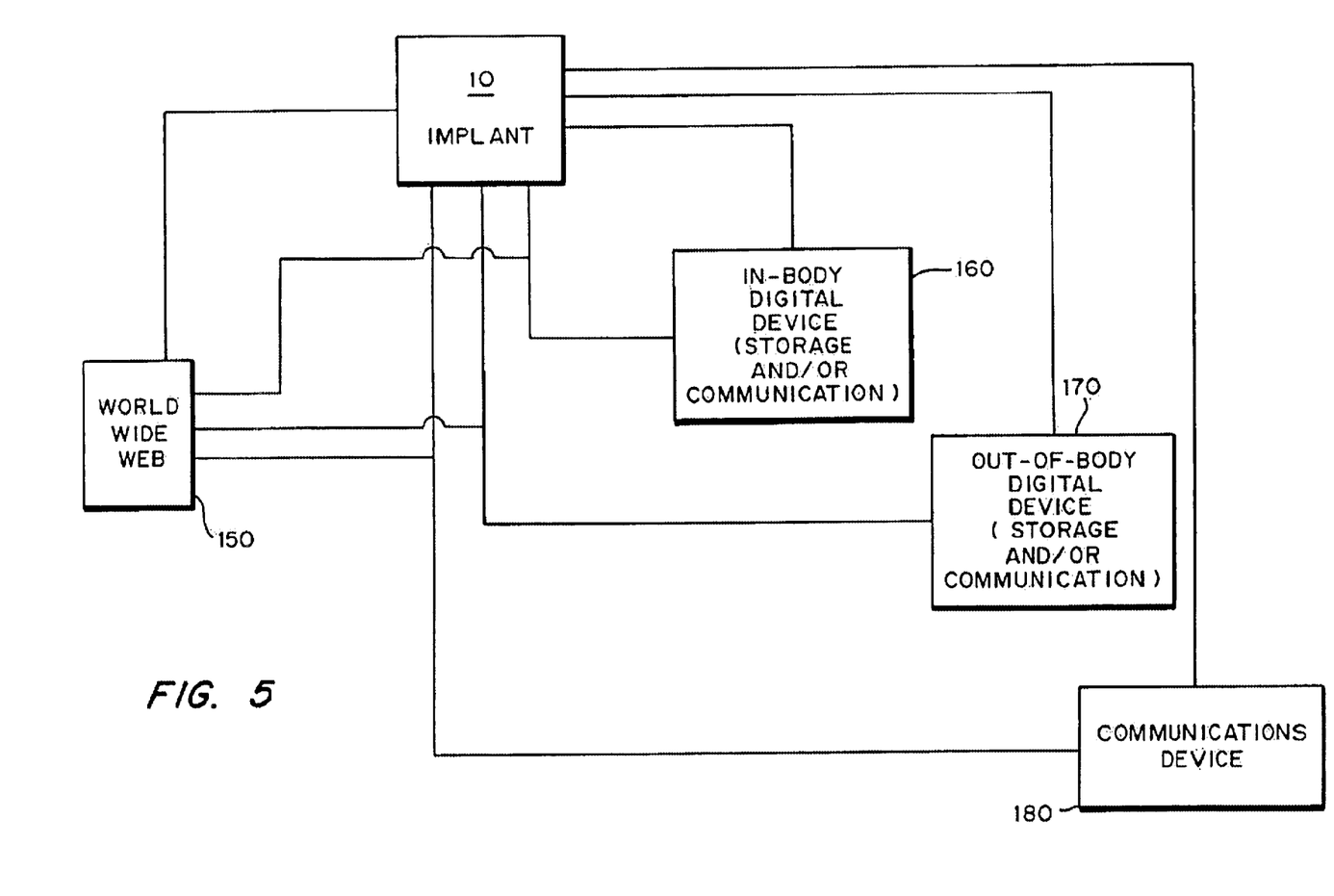
FIG. 5 is a schematic diagram of the implant, the in-body digital device, the out-of-body digital device, a communication device and the world wide web.

As shown in FIG. 5, implant (10), in-body digital device (160), out-of-body digital device (170), and communications device (180) communicate with implant (10) and with the world wide web (150), preferably by posting to a web page (not shown). This might be referred to as a "nested loop". In another embodiment, in-body digital device (160), out-of-body digital device (170), and communications device (180) all communicate with each other as well (not shown). These communications can encompass information received from the sensors (not shown) associated with the implant (10), as well as commands given to the actuator (not shown) of the implant (10).

F. Drugs and Drug Releasing Means

Any natural or synthetic, organic or inorganic molecule or mixture thereof can be delivered. In one embodiment, the implant is used to deliver drugs systemically to a patient in need thereof. In another embodiment, the construction and placement of the implant in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. The drugs can be in the form of a single drug or drug mixtures and can include pharmaceutically acceptable carriers. In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents. U.S. Pat. No. 5,797, 898 to Santini, et al., describes implants for delivery of a wide variety of molecules. Implant or implants are miniaturized devices constructed using methods commonly applied to the manufacture of integrated circuits such as ultraviolet (UV) photolithography, reactive ion etching, and electron beam evaporation. The implants provide control over the rate the molecules are released as well as the time at which release begins. The time of release can be controlled passively or actively.

In the simplest of the embodiments described herein, the implant is formed of a material which is itself responsive to the environment, for example, to temperature or pH, which causes a change in the material, for example, an increase in pore size, thereby effecting release of the bioactive, prophylactic or diagnostic agent as needed. An example of such a situation is when the tissue around the implant becomes infected, thereby changing both the temperature and the pH. Use of a temperature responsive material that increases porosity as the temperature increases can be used to deliver antibiotic only when, or in an increased amount when, infection is present.

G. Devices for Treating Chronic Cardiac Contractile Dysfunction

The micromachine actuators described herein can also be used to support or reinforce heart wall muscle in patients with congestive heart failure. These devices are implanted into the heart muscle, and contains both sensor and actuator means that synchronize expansion and contraction of devices secured to the heart wall muscle with the contraction and expansion of the normal, but impaired heart wall. By assisting the heart to function, patients that otherwise would die are provided with relief from the symptoms of the disease, including fluid on the lungs or fluid in the belly, liver and legs.

Modifications and variations of the forgoing devices and methods of use will be obvious to those skilled in the art and are intended to come within the scope of the following claims. The teachings of the cited references are specifically incorporated herein.

I claim:

1. A system for monitoring and responding to the environment of an implanted device comprising:
   one or more sensors configured for monitoring data relating to variables selected from the group consisting of electrical, magnetic, mechanical, fluid flow, chemical, and thermal properties in the device or its environment in a patient,
   at least one actuator configured for implementing a response to the monitored data in the device by causing a configurational change in the device; and
   means for communication selected from the group consisting of a means for communication to one of a series of nested loops of information exchange, monitoring means configured for positioning external to the patient, an external input connected through loops to effectuate change in the device from the at least one actuator, transmitting and receiving means to the one or more sensors and means for remotely accessing the data;
   wherein the one or more sensors directly interact with the device through the at least one actuator such that data transmitted from the one or more sensors to the at least one actuator causes a configurational change in the device.

2. The system of claim 1 which includes a data storage means.

3. The system of claim 2 wherein the data storage means is configured to be placeable on the device or contiguous to the device or within or on the body of the patient.

4. The system of claim 1 which includes a telemetry means.

5. The system of claim 4 wherein the telemetry means is an analog or digital electronic device.

6. The system of claim 1 comprising means for communication to one of a series of nested loops of information exchange.

7. The system of claim 1 comprising an external input connected through loops to effectuate change in the device from the at least one actuator.

8. The system of claim 1 additionally comprising monitoring means configured for positioning external to the patient.

9. The system of claim 1 wherein the sensor is configured to detect changes in pH, temperature, ion concentration, or analyte concentration.

10. The system of claim 1 comprising transmitting and receiving means to the one or more sensors.

11. The system of claim 1 comprising means for remotely accessing the data.

12. The system of claim 1 wherein at least one sensor is connected to means for transmitting or receiving data from a computer or phone communication means.

13. A system for monitoring and responding to the environment of an implanted device comprising
   one or more sensors configured for monitoring data relating to variables selected from the group consisting of electrical, magnetic, mechanical, fluid flow, chemical, and thermal properties in the device or its environment in a patient, and
   at least one actuator configured for implementing a response to the monitored data in the device by causing a configurational change in the device;
   wherein the one or more sensors directly interact with the device through the at least one actuator such that data transmitted from the one or more sensors to the at least one actuator causes a configurational change in the device wherein at least one sensor is configured to measure fouling of the device or at least one sensor over time.

14. The system of claim 13 wherein at least one sensor is configured to measure protein deposition or formation of a bacterial film on a biliary stent, increase in calcification of a urinary stent, and neointimal thickening of an arterial stent, resulting in an increase in thickness, mass and wall shear.

15. A system for monitoring and responding to the environment of an implanted device comprising:
   one or more sensors configured for monitoring data relating to variables selected from the group consisting of electrical, magnetic, mechanical, fluid flow, chemical, and thermal properties in the device or its environment in a patient, and at least one actuator configured for implementing a response to the monitored data in the device by causing a configurational change in the device;

wherein the one or more sensors directly interact with the device through the at least one actuator such that data transmitted from the one or more sensors to the at least one actuator causes a configurational change in the device comprising:

(a) one or more sensors for monitoring the general environment of the implanted device;

(b) monitoring means; and (c) the one or more sensors configured for communicating information to the monitoring means and to each other, and configured for communicating commands to the actuator.

16. The system of claim 15 wherein the one or more sensors communicate information to a computer transmitting the information to another computer via the internet.

17. The system of claim 16 wherein the transmission over the Internet to another computer is via a posting to the world wide web.

18. An implantable device comprising:

one or more sensors configured for monitoring at least one condition;

at least one actuator configured for implementing a response to the monitored condition in the device by causing a configurational change in the device; and means for communication to one of a series of nested loops of information exchange;

wherein the one or more sensors directly interact with the device through the at least one actuator such that data transmitted from the one or more sensors to the at least one actuator causes a configurational change in the device; and the one or more sensors and the at least one actuator are configured for control by at least one apparatus external to the implantable device.

* * * * *